US011250931B2

(12) United States Patent
Locke

(10) Patent No.: US 11,250,931 B2
(45) Date of Patent: Feb. 15, 2022

(54) SYSTEMS AND METHODS FOR DETECTING RECOMBINATION

(71) Applicant: Seven Bridges Genomics Inc., Cambridge, MA (US)

(72) Inventor: Devin Locke, Medford, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 794 days.

(21) Appl. No.: 15/254,258

(22) Filed: Sep. 1, 2016

(65) Prior Publication Data

US 2018/0060480 A1    Mar. 1, 2018

(51) Int. Cl.
| | | |
|---|---|---|
| *G01N 33/48* | (2006.01) | |
| *G16B 20/20* | (2019.01) | |
| *G16H 50/50* | (2018.01) | |
| *G16B 20/00* | (2019.01) | |
| *G16B 30/00* | (2019.01) | |
| *G16B 30/10* | (2019.01) | |

(52) U.S. Cl.
CPC ............ *G16B 20/20* (2019.02); *G16B 20/00* (2019.02); *G16B 30/00* (2019.02); *G16B 30/10* (2019.02); *G16H 50/50* (2018.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,988,617 A | 1/1991 | Landegren et al. | |
| 5,234,809 A | 8/1993 | Boom et al. | |
| 5,242,794 A | 9/1993 | Whiteley et al. | |
| 5,494,810 A | 2/1996 | Barany et al. | |
| 5,511,158 A | 4/1996 | Sims | |
| 5,583,024 A | 12/1996 | McElroy et al. | |
| 5,674,713 A | 10/1997 | McElroy et al. | |
| 5,700,673 A | 12/1997 | McElroy et al. | |
| 5,701,256 A | 12/1997 | Marr et al. | |
| 6,054,278 A | 4/2000 | Dodge et al. | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,582,938 B1 | 6/2003 | Su et al. | |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,321,623 B2 | 1/2008 | Dambrackas | |
| 7,483,585 B2 | 1/2009 | Brakus, Jr. | |
| 7,577,554 B2 | 8/2009 | Lystad et al. | |
| 7,580,918 B2 | 8/2009 | Chang et al. | |
| 7,598,035 B2 | 10/2009 | Macevicz | |
| 7,620,800 B2 | 11/2009 | Huppenthal et al. | |
| 7,776,616 B2 | 8/2010 | Heath et al. | |
| 7,809,509 B2 | 10/2010 | Milosavljevic | |
| 7,835,871 B2 | 11/2010 | Kain et al. | |
| 7,885,840 B2 | 2/2011 | Sadiq et al. | |
| 7,917,302 B2 | 3/2011 | Rognes | |
| 7,957,913 B2 | 6/2011 | Chinitz et al. | |
| 7,960,120 B2 | 6/2011 | Rigatti et al. | |
| 8,146,099 B2 | 3/2012 | Tkatch et al. | |
| 8,165,821 B2 | 4/2012 | Zhang | |
| 8,209,130 B1 | 6/2012 | Kennedy et al. | |
| 8,340,914 B2 | 12/2012 | Gatewood et al. | |
| 8,370,079 B2 | 2/2013 | Sorenson et al. | |
| 8,639,847 B2 | 1/2014 | Blaszczak et al. | |
| 8,972,201 B2 | 3/2015 | Mande et al. | |
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,817,944 B2 | 11/2017 | Kural | |

(Continued)

FOREIGN PATENT DOCUMENTS

| | | |
|---|---|---|
| KR | 101282798 B1 | 7/2013 |
| WO | 2007/086935 A2 | 8/2007 |
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |

(Continued)

OTHER PUBLICATIONS

Standish (Data Structures, Algorithms and Software Principles in C, 1995 by Addison Wesley Publishing Company, Inc; see Chapter 10, sections 10.4-10.6).*

(Continued)

*Primary Examiner* — Anna Skibinsky

(74) *Attorney, Agent, or Firm* — Wolf, Greenfield & Sacks, P.C.

(57) ABSTRACT

A method for screening for disease in a genomic sample is includes receiving a representation of a reference genome comprising a sequence of symbols. The presence of a predicted mutational event is identified in a location of the reference genome. An alternate path is created in the reference genome representing the predicted mutational event. A plurality of sequence reads are obtained from a genomic sample, wherein at least one sequence read comprises at least a portion of the predicted mutational event. The at least one sequence read is then mapped to the reference genome and a location is determined corresponding to the predicted mutational event. The predicted mutational event is then identified as present in the genomic sample. The method may be used to detect evidence of non-allelic homologous recombination (NAHR) occurring in genomic samples.

19 Claims, 13 Drawing Sheets

Specification includes a Sequence Listing.

(56) References Cited

U.S. PATENT DOCUMENTS

| | | |
|---|---|---|
| 2002/0164629 A1 | 11/2002 | Quake et al. |
| 2002/0190663 A1 | 12/2002 | Rasmussen |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0003571 A1 | 1/2008 | McKernan et al. |
| 2008/0077607 A1 | 3/2008 | Gatawood et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0124573 A1 | 5/2013 | Seth et al. |
| 2013/0232480 A1 | 9/2013 | Winterfeldt et al. |
| 2013/0289099 A1 | 10/2013 | Goff et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1* | 12/2015 | Mishra .............. G06F 16/24575 707/693 |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Standish (Data Structures, Algorithms and Software Principles in C, 1995 by Addison Wesley Publishing Company, Inc; see pp. 35-36 and 412-413).*

Schneeberger, Korbinian, et al. "Simultaneous alignment of short reads against multiple genomes." Genome biology 10.9 (2009): R98.*

Wajid, Bilal, and Erchin Serpedin. "Review of general algorithmic features for genome assemblers for next generation sequencers." Genomics, proteomics & bioinformatics 10.2 (2012): 58-73.*

Parks, Matthew M., Charles E. Lawrence, and Benjamin J. Raphael. "Detecting non-allelic homologous recombination from high-throughput sequencing data." Genome biology 16.1 (2015): 72.*

The Variant Call Format (VCF) Version 4.2 Specification (Jan. 26, 2015), available at https://samtools.github.io/hts-specs/VCFv4.2.pdf.

Thomas, 2014, Community-wide effort aims to better represent variation in human reference genome, Genome Web (11 pages).

Torri, 2012, Next generation sequence analysis and computational genomics using graphical pipeline workflows, Senes (Basel) 3(3):545-575.

Trapnell, 2009, TopHat: discovering splice junctions with RNA-Seq, Bioinformatics 25:1105-1111.

Trapnell, 2010, Transcript assembly and abundance estimation from RNA-Seq reveals thousands of new transcripts and switching among isoforms, Nat Biotech 28(5):511-515.

Trapnell, 2010, Transcript assembly and quantification by RNA-Seq reveals unannotated transcripts and isoform switching during cell differentiation, Nat Biotech 28(5):511-515.

(56) References Cited

OTHER PUBLICATIONS

Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetrapioid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break-Understanding and Combating Decay in Taverna Workflows, eScience 2012, Chicago, Oct. 2012.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 200/, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
Duan et al., Optimizing de novo common wheat transcriptome assembly using short-read RNA-Seq data. (2012) pp. 1-12, vol. 13, BMC Genomics.
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
International Search Report and Written Opinion dated Aug. 31, 2017, for International Application No. PCT/US2017/018830 with International Filing Date Feb. 22, 2017, (11 pages).
International Search Report and Written Opinion dated Apr. 19, 2017 for International Patent Application No. PCT/US2017/012015, (14 Pages).
International Search Report and Written Opinion dated Apr. 7, 2017, for International Patent Application No. PCT/US17/13329, filed Jan. 13, 2017, (9 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, (11 pages).
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Marth et al., 1999—A general approach to single-nucleotide polymorphism discovery, pp. 452-456, vol. 23, Nature Genetics.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Zeng, 2013, PyroHMMvar: a sensitive and accurate method to call short indels and SNPs for Ion Torrent and 454 data, Bioinformatics 29:22 2859-2868.

(56) References Cited

OTHER PUBLICATIONS

Zhang et al., Construction of a high-density genetic map for sesame based on large scale marker development by specific length amplified fragment (SLAF) sequencing. (2013) pp. 1-12, vol. 13, BMC Plant Biology.
Oshlack, 2010, From RNA-seq reads to differential expression results. Genome Bio 11:220.
Pabinger, 2013, A survey of tools for variant analysis of next-generation genome sequencing data, Brief Bioinf.
Parks, 2015, Detecting non-allelic homologous recombination from high-throughput sequencing data, Genome Biol 16:17.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Popitsch, 2013, NGC: lossless and lossy compression of aligned high-throughput sequencing data, Nucl Acids Res, 41(1):e27.
Posada, 1998, Model Test: testing the model of DNA substitution, Bioinformatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Mucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing-pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res41(17):e162.
Tan, 2010, A Comparison of Using Tavema and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
Tewhey, 2011, The importance of phase information for human genomics, Nat Rev Gen 12:215-223.
The 1000 Genomes Project, 2015, A global reference for human genetic variation, Nature 526:68-74.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.

(56) References Cited

OTHER PUBLICATIONS

Bao, 2013, BRANCH: boosting RNA-Seq assemblies with partial or related genomic sequences, Bioninformatics 29(10):1250-1259.
BCF2 Quick Reference (Γ198), available at http://samtools.github.io/hts-specs/BCFv2_qref.pdf.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chen, 2014, Genome architecture and its role in human copy number variation, Genomics Inform 12(4):136-144.
Chin, 2013, Nonhybrid finished microbial genome assemblies from long-read SMRT sequencing data, Nat Meth 10 (6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12):e1000589.
Durbin, 2014, Efficient haplotype matching and storage using the positional Burrows-Wheeler transform (PBWT), Bioinformatics 30(9):1266-1272.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29 (7):644-654.
Grasso, 2004, Combining partial order alignment and progressive multiple sequence alignment increases alignment speed and scalability to very large alignment problems, Bioinformatics 20(10):1546-1556.
Gullmnan, 2010, Ab initio reconstruction of cell type-specific transcriptomes in mouse reveals the conserved multi-exonic structure of lincRNAs, Nat Biotech 28(5):503-510.
Gullmnan, 2010, Ab initio reconstruction of transcriptomes of pluripotent and lineage committed cells reveals gene structures of thousands of lincRNAs, NIH-PA Author Manuscript.
Layer, 2015, Efficient compression and analysis of large genetic variation datasets, Biorxiv preprint, available at http://biorxiv.org/content/early/2015/04/20/018259.
Layer, 2015, Efficient genotype compression and analysis of large genetic-variation data sets, Nat Meth 13(1):63-65.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Mosaik: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Tavema workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Li, 2015, BGT: efficient and flexible genotype query across many samples, arXiv: 1506.08452 [q-bio.GN].

(56) References Cited

OTHER PUBLICATIONS

Li, 2015, Towards Better Understanding of Artificats in Variant Calling from High-Coverage Samples, arXiv:1404.0929 [q-bio.GN].
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693): 1435-41.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology-EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectial partitioning of random graphs, Proc 42nd IFFF Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation Practice and Experience 18(10):1067-1100.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8): 1904-1915.
Horspool, 1980, Practical Fast Searching in Strings, Software-Practice & Experience 10:501-506.
Huang, Chapter 3: Bio-Sequence Comparison and Alignment, ser. CurrTop Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for application No. PCT/US16/57324 with International filing date Oct. 17, 2016 (7 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).

(56) References Cited

OTHER PUBLICATIONS

International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application Mo. PCT/US14/52065, filed Aug. 21, 2014, (18 pages).
International Search Report and Written Opinion dated Dec. 30, 2014, for International Patent Application Mo. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 tor International Application No. PCT/US2015/048891 (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Krabbenhoft, 2008, Integrating ARC grid middleware with Taverna workflows, Bioinformatics 24(9):1221-2.
Kuhn, 2010, CDK—Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.

\* cited by examiner

↙ 201

5'...CCCAGAACGTTGCAAGGGACAAACGTTGCCATGCCC...3'
(SEQ ID NO: 1)

5'...AACGTTGC...3'

5'...CCCAG AACGTTGC AAGGGACAAACGTTGCCATGCCC...3'
(SEQ ID NO: 1)

SEQUENCE LISTING

<160> NUMBER OF SEQ ID NOS: 3

<210> SEQ ID NO 1
<211> LENGTH: 36
<212> TYPE: DNA
<213> ORGANISM: Homo sapiens

<400> SEQUENCE: 1
cccagaacgt tgcaagggac aaacgttgcc atgccc                                36

<210> SEQ ID NO 2
<211> LENGTH: 16
<212> TYPE: DNA
<213> ORGANISM: Homo sapiens

<400> SEQUENCE: 2
aagggacaaa cgttgc                                                      16

<210> SEQ ID NO 3
<211> LENGTH: 15
<212> TYPE: DNA
<213> ORGANISM: Homo sapiens

<400> SEQUENCE: 3
aacgttgcca tgccc                                                       15

SYSTEMS AND METHODS FOR DETECTING RECOMBINATION

TECHNICAL FIELD

The invention relates to medical genetics.

BACKGROUND

Birth defects such as congenital heart disease, learning disabilities, and recurrent infections are sometimes associated with genetic conditions such as DiGeorge syndrome. Di George syndrome is characterized by a three megabase deletion from chromosome 22q11. That deletion is thought to be caused by non-allelic homologous recombination (NAHR). Homologous recombination is a mechanism by which cells repair double-strand DNA breaks. After a double-strand break the 5' ends are cut away in a process called resection. The overhanging 3' end anneals to a similar, unbroken DNA segment in a process called invasion. The DNA molecule is then repaired via the cell machinery. When homologous recombination occurs during meiosis, it involves a crossover between sister chromosomes, producing new combinations of genes in gametes and increased genetic variation in the offspring.

However, homologous recombination sometimes operates on unintended regions of the genome, which may lead to merging of distant sections of the genome. For example, in NAHR, genetic recombination occurs between similar DNA segments that are not alleles. NAHR usually occurs between sequences of DNA that have been previously duplicated, such as Low Copy number Repeat (LCR) regions of the genome. LCRs are repetitive elements that extend over several kilobases (typically 10-300 kb) and share significant (e.g., >95%) sequence identity. Due to the sequence similarity in those regions, NAHR may cause genomic rearrangements, commonly in the form of a deletion of the nucleotide sequence between the two LCRs (typically 10-50 kb). However, other events may occur, including duplications, inversions, and translocations.

SUMMARY

The invention provides systems and methods that detect evidence of NAHR in a subject by comparing genetic sequences from the subject to a reference genome in which possible NAHR events have been predicted and represented as links between segments with high sequence similarity. A computer system is used to scan through the reference genome and find putative homologous segments, i.e., a first segment and a second segment that are highly similar to each other. An object is created in memory of the system that represents a link from the first segment to the second segment, which link would be the genome that would remain were NAHR to occur between the two segments and cause a deletion of the intervening sequence. The system performs an alignment between the genetic sequence from the subject and reference. When the sequence aligns best across the object representing the link, the alignment is evidence of NAHR and the associated deletion in the genome of the subject. The system then provides a report for the subject that may include a description of the deletion or any associated medical condition.

In some embodiments, the reference is initially a genomic graph that represents variation in a population. In a genomic graph, genomic information for one individual can be read by tracing a path through the graph. The genomic graph branches into multiple paths in the instance where individuals in the population exhibit genetic variation, wherein the multiple paths include one path for each variant genome. The genomic graph improves the system relative to traditional genetic analysis with flat-file reference genomes because the graph may be stored in the memory using objects wherein connections between the objects are shown within the objects themselves using pointers that describe the physical location in the memory of any adjacent object. Thus when the system finds a new putative homologous segment, the system can represent the indicated NAHR event by adding a link from one object (for the first segment) to a second object (for the second genomic segment), wherein the link uses a pointer to a physical location in the memory of the second object. This makes the second object adjacent to the first object. If the NAHR event has occurred in the subject, that adjacency represents the actual adjacency of the two segments (recombined into one) within the subject genome. For any given object in the graph, all adjacent objects in the memory may be indicated through the use of an adjacency list in the given object. Because the objects are linked by pointers to physical locations in the memory, the system can perform operations on the graph very rapidly, where those operations would otherwise require costly look-up time in an index or other such intermediating database structure. Thus the invention leverages a feature that is implemented at a low-level, or hardware level (adjacency lists and physical pointers) to vastly improve the analysis of information significant to medical genetics.

In certain aspects, the invention provides a method of detecting a recombination. The method includes providing a genomic reference stored as one or more objects in tangible, non-transitory memory coupled to a processor and identifying within the genomic reference, using the processor, a first segment and a second segment that are homologous to each other. An object connecting the first segment to the second segment is created and stored in the memory. The method includes aligning sequences from a subject to the first segment and the second segment and providing a report describing a recombination event in the subject when the sequences align across the object. In preferred embodiments, the genomic reference is provided as a graph representing at least a substantial portion of a human genome and known variants of the human genome. The graph may be a directed acyclic graph comprising connected objects, in which portions of a genome are stored as strings of characters in the objects. The method may include finding a plurality of low copy repeats, each low copy repeat comprising a pair of homologous segments, and creating an additional object in the genomic reference connecting each pair of homologous segments.

The sequences may be aligned by an operation that includes assigning a score to each of multiple alternative paths through the genomic reference for the sequences. In some embodiments, the sequences from the subject are sequence reads and the method comprises sequencing nucleic acid from the subject to generate the sequence reads.

Methods may include identifying two segments as homologous to each other based on a threshold similarity. For example, the first segment and the second segment may be identified as homologous to each other when they have at least about 90% sequence similarity. In some embodiments, the first segment and the second segment are identified as homologous to each other only if the distance along the genomic reference between the first segment and the second segment is between 10 kilobases and 300 kilobases. The identifying step may include a sliding window operation that includes reading a string of N bases from the genomic reference and aligning the string to the genomic reference to determine that the first segment is homologous to the second segment. Specifically, the method may include reading a second string of bases offset along the genomic reference from the string of N bases and performing an alignment between the second string of bases and the genomic reference. Additionally, the method may include iteratively sliding a window of length N to a plurality of positions along the genomic reference and, for each position, finding alignments between a string from a current position and the genomic reference. Additionally or alternatively, methods may include identifying homologous segments using extrinsic information. For example, in some embodiments, the first segment and the second segment are identified from a database of known repeats.

Methods may be used to provide a report that identifies a medical condition associated with the recombination. The report may identify one or more deletions in a genome of the subject.

Aspects of the invention provide a method of screening for disease in a genomic sample. The method includes receiving—using at least one computer hardware processor—a representation of a reference genome, the reference genome comprising a sequence of symbols, the receiving comprising storing the reference genome in at least one object in computer memory and identifying the presence of a predicted mutational event in a location of the reference genome. Using the processor, the method includes creating an alternate path in the reference genome representing the predicted mutational event, the creating comprising segmenting the reference genome at the location of the predicted mutational event, creating a first path connecting the segmented reference genome, and creating a second path connecting at least part of the segmented reference genome with the predicted mutational event. The method further includes obtaining a plurality of sequence reads from a genomic sample (e.g., wherein at least one sequence read comprises at least a portion of the predicted mutational event) and mapping the sequence reads to the reference genome by determining a location on the reference genome for which a score for the at least one sequence read is maximized. The determined location of the mapped at least one sequence read spans the alternate path representing the predicted mutational event. The method includes identifying the predicted mutational event as present in the genomic sample. Identifying the presence of a predicted mutational event in a location of the reference genome may include accessing information specifying the presence of the predicted mutational event. In some embodiments, accessing information specifying the presence of the predicted mutational event includes accessing a database of predicted mutations.

Preferably the representation of the reference genome is a graph such as a directed acyclic graph (DAG). A representation of a reference genome in the form of a DAG may be referred to as a genomic reference DAG. A genomic reference DAG may be stored in tangible memory using adjacency lists or index-free adjacency to support a very rapid form of a modified Smith-Waterman alignment as well as other rapid graph traversals. Similarly, a genomic reference DAG may be stored as a set of objects, each object having a set of parent objects, an identifier, and an associated sequence.

An alignment operation with a genomic reference DAG is particularly rapid for at least two reasons. First, when considering two aligned loci, finding and comparing the possible neighboring loci does not require a look-up in an index and instead requires only following a pointer provided within an adjacency list to read a value from an indicated location (the pointer points to a physical location in memory at which the adjacent object is stored). Second, stretches of conserved genome in the reference can each be represented by a single node or edge object in the genomic reference graph, such that the object includes a full string of nucleotide characters to represent the conserved stretch. Thus when the system is traversing the genomic reference, it only needs to perform a look-up to a new location when it reaches the end of such a string of characters.

In certain embodiments, identifying the presence of a predicted mutational event involves predicting the presence of the mutational event. For example, the predicted mutational event may be determined computationally by scanning the reference genome. Predicting the presence of the mutational event may include identifying a first and a second segment of the reference genome that are homologous (e.g., where the first segment and the second segment have more than 90% sequence similarity, are separated by a distance of between 10 kilobases and 300 kilobases, or both).

Segmenting the reference genome at the location of the predicted mutational event may include segmenting the reference genome into a first segment, a second segment, and a third segment, and associating each of the segments with respective first, second, and third objects in computer memory. Creating the alternate path in the reference genome representing the predicted mutational event may include associating the predicted mutational event with a fourth object in computer memory. Creating a first path connecting the segmented reference genome may include connecting the first, second, and third objects into the first path. Additionally, creating a second path connecting at least part of the segmented reference genome with the predicted mutational event may include connecting the first, fourth, and third objects into the second path. The first segment and the third segment are homologous, i.e., have more than 90% sequence similarity. Preferably, the second segment comprises a nucleotide sequence of between 5 kilobases and 100 kilobases. The second path represents a deletion of the second segment or a recombination event in the reference genome.

The method may include identifying a medical condition in the genomic sample associated with the predicted mutational event.

In some aspects, the invention provides a system for detecting a recombination. The system includes tangible, non-transitory memory coupled to a processor with a genomic reference stored as one or more objects in the memory. The system further includes instructions that, when executed by the processor, cause the system to (i) identify within the genomic reference a first segment and a second segment that are homologous to each other, (ii) create an object connecting the first segment to the second segment and storing the object in the memory, (iii) align sequences from a subject to the first segment and the second segment, and (iv) provide a report describing a recombination event in the subject when the sequences align across the object. The genomic reference may be provided as a graph (e.g., as a genomic reference DAG) representing at least a substantial portion of a human genome and known variants of the human genome. In some embodiments, the graph is a directed acyclic graph comprising connected objects, with portions of a genome stored as strings of characters in the objects. The sequences are aligned by an operation that includes assigning a score to each of multiple alternative paths through the genomic reference for the sequences.

In some embodiments, the sequences from the subject are sequence reads and the system comprises a nucleic acid sequencing instrument such as a an NGS instrument sold under the trademark HISEQ by Illumina for sequencing nucleic acid from the subject to generate the sequence reads.

The system can identify homology based on similarity or relative genomic location. In some embodiments, the system identifies the first segment and the second segment as homologous to each other when they comprises at least about 90% sequence similarity. The first segment and the second segment may be identified as homologous to each other only if the distance along the genomic reference between the first segment and the second segment is between 10 kilobases and 300 kilobases.

The report may identify a medical condition associated with the recombination, deletions in a genome of the subject, or both.

The system may be operable to find a plurality of low copy repeats, each low copy repeat comprising a pair of homologous segments, and create an additional object in the genomic reference connecting each pair of homologous segments.

In some aspects, the invention provides a system for screening for disease in a genomic sample. The system includes tangible, non-transitory memory coupled to a processor. The memory includes, stored as an object within, a representation of a reference genome that includes a sequence of symbols.

The system further includes instructions that, when executed by the processor, cause the system to identify the presence of a predicted mutational event in a location of the reference genome; create an alternate path in the reference genome representing the predicted mutational event, the creating comprising segmenting the reference genome at the location of the predicted mutational event, creating a first path connecting the segmented reference genome, and creating a second path connecting at least part of the segmented reference genome with the predicted mutational event; obtain a plurality of sequence reads from a genomic sample, wherein at least one sequence read comprises at least a portion of the predicted mutational event; map the at least one sequence read to the reference genome, the mapping comprising determining a location on the reference genome for which a score for the at least one sequence read is maximized, wherein the determined location of the mapped at least one sequence read spans the alternate path representing the predicted mutational event; and identify the predicted mutational event as present in the genomic sample.

BRIEF DESCRIPTION OF THE DRAWINGS

FIG. 2 illustrates a genomic reference.

FIG. 8 shows the matrices that represent an aligning to a graph.

FIG. 12 illustrates a sliding window method for identifying homologous segments.

DETAILED DESCRIPTION

Figure 1:
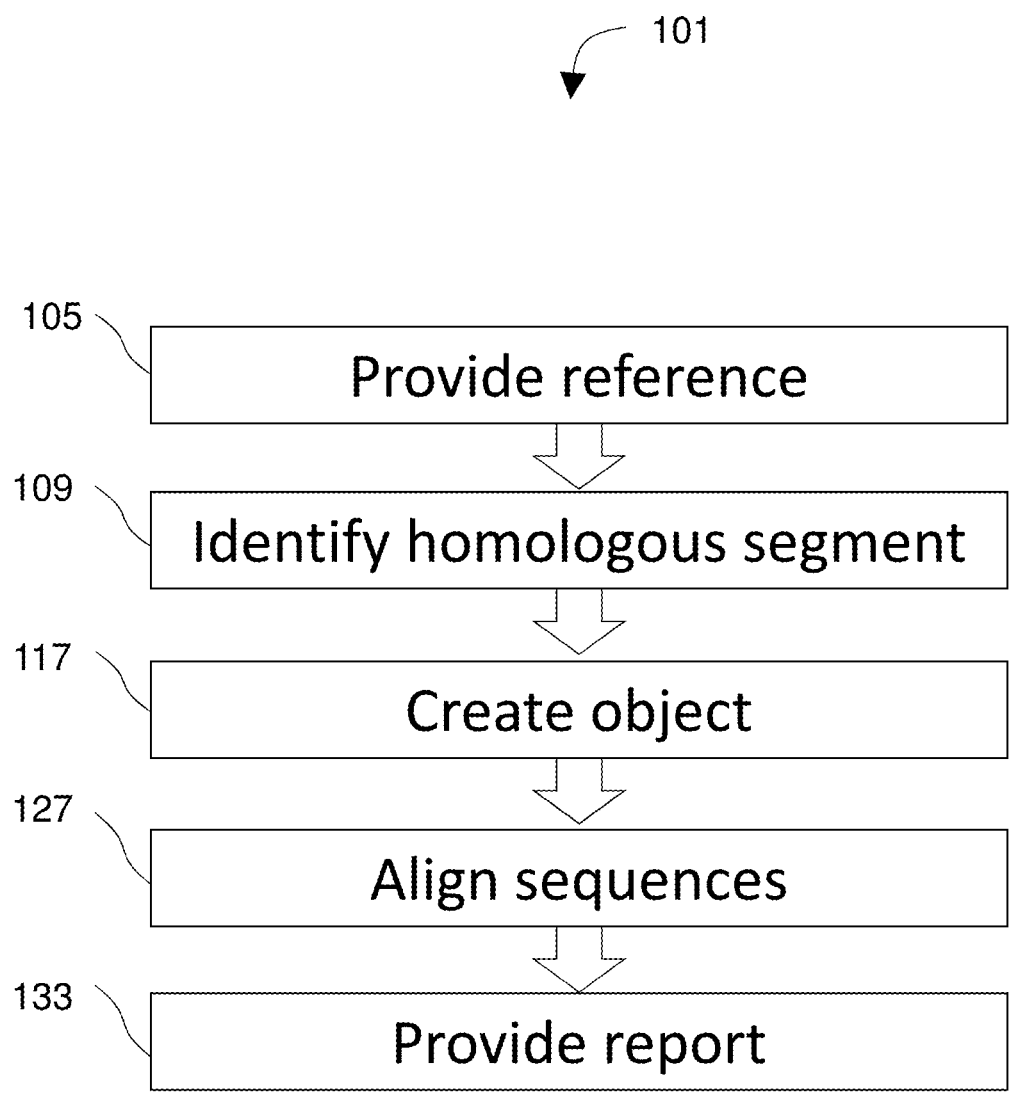
FIG. 1 diagrams steps of a method of detecting a recombination.

Embodiments of the invention may be used for identifying unknown NAHR events with whole genome sequencing. NAHR events may occur at various positions within a genome, and whole genome sequencing techniques may be useful for the detection of NAHR events. However, the identification of NAHR events in patient genomes using conventional genomics and bioinformatics techniques is subject to several complications. Sequence reads generated using next-generation sequencing are relatively short (e.g., 50-200 bp), and therefore more amenable to identifying short variations of a few base pairs. Alignment tools may not be able to align sequence reads that span an NAHR deletion, and a subsequent variant calling step may miss the deletion entirely, or mark it as simply a low coverage or un-sequenced region. Software packages exist to find changes in gene copy number or to locate larger structural variants and deletions; however, these tools rely on the underlying alignment, which due to the NAHR event may be flawed. See Colnaghi et al., 2011, The Consequences of Structural Genomic Alterations in Humans: Genomic Disorders, Genomic Instability, and Cancer, Stem Cell Dev Bio 22:875-885 and Koolen et al, 2008, Clinical and Molecular Delineation of the 17q21.31 Microdeletion Syndrome, J Med Gen 45(11):710-720, both incorporated by reference.

Systems and methods of the invention may be used to detect NAHR events in a subject by analyzing sequences such as the short reads produced by next-generation sequencing (NGS) technologies. Those sequences are analyzed against a reference in which graph principles are used to represent predicted, possible NAHR events. Specifically, a reference genome, or genomic reference graph, is analyzed for pairs of homologous segments. When such a pair is identified, the possible results of NAHR (including a deletion of the intervening sequence between the homologous segments, a duplication, or an inversion) may be added to the reference genome as an additional object or set of objects. For example, in the case of a deletion, an object may be used to connect the first homologous segment to the second homologous segment. The connection from the first homologous segment to the second homologous segment means that the reference has graph properties in that one can trace one of at least two alternative paths between the two segments. One of the alternative paths follows the original reference genome, e.g., the "backbone branch" of the graph. Another of the alternative paths travels directly from the first segment to the second segment, thus representing a deletion of the intervening sequence between the two segments. Because the ability to trace alternative paths through sets of connected objects is provided by the graph, the genetic analysis can be coupled to graph-specific implementations of the reference, such as the use of adjacency lists to link components of the reference. Thus, when NGS reads are aligned to the reference, systems and methods of the invention proceed very rapidly in tracing through all branches of the reference and finding the best alignment. When those reads best align across an object that was created to connect a homologous pair of segments found in the original reference, the system can report that the subject from which those reads were generated is missing a chromosomal segment, relative to the reference, between those homologous pairs.

For example, 17q21.31 microdeletion syndrome is a condition with phenotypic features including developmental delay, hypotonia, and facial dysmorphisms. This disorder is thought to affect 1 in 16,000 people. The microdeletion at issue may be the product of NAHR. Using systems and methods described herein, a microdeletion can be detected and reported in a subject. NAHR is thought to be involved in a variety of significant health and medical problems. NAHR may lead to gene fusion and gene interruption rearrangements, resulting in various positional effects, or revealing recessive alleles. Further, NAHR events may also have a reciprocal, corresponding duplication.

Graphs such as directed acyclic graphs (DAGs) may be used as data structures for associating genome sequence data and variation. In some embodiments, graphs have a reference sequence (such as the nucleotide sequence of a genome or chromosome) as the base or backbone branch. Variations, such as SNPs, indels, and larger structural variants are then appended to the base branch as new edges, defining new paths that include the variation. Sequence reads may then be aligned to the graph instead of a linear reference sequence. Because the graph includes known variation, sequence alignment is improved and more sequence reads are aligned. However, building such a graph requires previous knowledge of variations.

Using methods and systems described herein, NAHR events can be accurately detected by populating a reference graph with computationally predicted NAHR events. In particular, NAHR events typically occur between closely situated LCRs on the same chromosome. This suggests an algorithm in which a reference graph may be pre-populated with NAHR events based on an analysis of the repetitive regions of each chromosome. The resulting reference graph thus includes nearly every possible NAHR event. To identify whether a patient's genome has experienced such an event, the patient's whole genome sequencing data is aligned against the reference graph structure. The reference graph may then be used during sequence alignment to confirm the existence of previously unknown NAHR events in patients, identifying all possible deletions, gene fusions, and the like.

FIG. 1 diagrams steps of a method 101 of detecting a recombination. The method 101 includes the steps of providing 105 a genomic reference stored as one or more objects in tangible, non-transitory memory coupled to a processor and identifying 109 within the genomic reference a first segment and a second segment that are homologous to each other. The method 101 includes creating 117 an object connecting the first segment to the second segment and storing the object in the memory and aligning 127 sequences from a subject to the first segment and the second segment. Additionally, the method 101 includes providing 133 a report describing a recombination event in the subject when the sequences align across the object.

FIG. 2 illustrates a genomic reference 201 that may be provided 105. The genomic reference 201 includes CCCAGAACGTTGCAAGGGACAAACGTTGC-CATGCCC (SEQ ID NO: 1). The ellipses indicate that the genomic reference 201 is larger than what is shown. In some embodiments, the genomic reference 201 includes all or a substantial part of a human genome or a chromosome of the human genome. A suitable human genome is, for example, GRCh37, the Genome Reference Consortium human genome (build 37) derived from thirteen anonymous volunteers from Buffalo, New York. The genomic reference 201 is stored using a system of the invention as one or more objects in tangible, non-transitory memory coupled to a processor.

Figure 3:
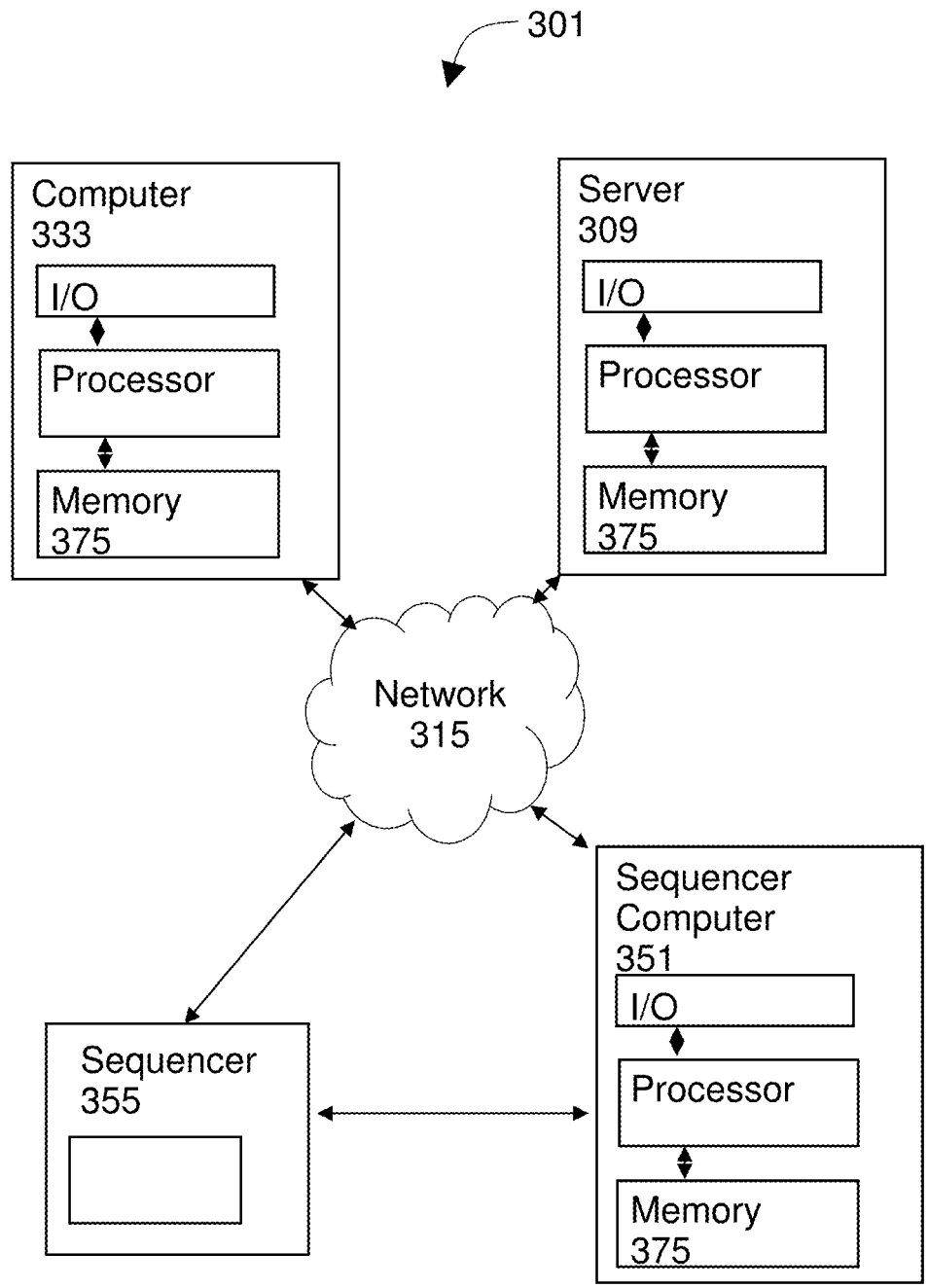
FIG. 3 diagrams a system for detecting recombination.

FIG. 3 diagrams a system 301 that includes at least one computer 333. The computer 333 includes a processor coupled to tangible, non-transitory memory 375 and one or more input/output (I/O) devices. The system 301 may include one or more the computer 333, a server computer 309, a sequencing instrument 355 coupled to a sequencing computer 351, or combinations thereof. Any of the computer 333, the server computer 309, the sequencing instrument 355, and the sequencing computer 351 may communicate via a communications network 315. Any of the computer 333, the server computer 309, and the sequencing computer 351 may be a computer. In general, a computer includes a processor coupled to memory and one or more input/output devices.

A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

Memory generally includes a tangible, non-transitory computer-readable storage device and can include any machine-readable medium or media on or in which is stored instructions (one or more software applications), data, or both. The instructions, when executed, can implement any or all of the functionality described herein. The term "computer-readable storage device" shall be taken to include, without limit, one or more disk drives, tape drives, flash drives, solid state drives (SSD), memory devices (such as RAM, ROM, EPROM, etc.), optical storage devices, and/or any other non-transitory and tangible storage medium or media.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Using the depicted elements (e.g., one or more processors coupled to a tangible, non-transitory memory 375), the system 301 is able to perform the steps of the method 101. For example, the system 301 may be used for identifying 109 within the genomic reference 201 a first segment and a second segment that are homologous to each other and creating 117 an object connecting the first segment to the second segment and storing the object in the memory 375. Thus, systems and methods of the invention may be used for populating a reference graph with predicted NAHR events.

Figure 4:
FIG. 4 illustrates identifying homologous segments.

FIG. 4 illustrates identifying 109 within the genomic reference 201 a first segment 403 and a second segment 409 that are homologous to each other. Systems and methods may first identify homologous segments (having in excess of 95% identity) of a particular chromosome. Homologous segments can be identified in many ways. For example, one could generate a self-alignment plot (or "dot-plot") of the sequence of the genomic reference 201. One common tool for generating self-alignment plots and alignments is YASS, publicly available at the Bonsai website provided by the Laboratoire d'Informatique Fondamentale de Lille. Self-alignments generated by YASS may be further evaluated to determine whether they are candidates for NAHR events.

This can be performed by evaluating the distance (e.g., 10-300 kb) between each candidate position in the self-alignment.

Similarly, homologous segments could be identified by using an alignment or sequence searching tool, such as BLAST or BLAT. The first N bases of the chromosome may be selected as input for the alignment tool, which then identifies regions of the chromosome with sufficient identity. The positions and number of each homologous region are noted. The window may then be shifted by an additional number of bases and the process repeated. Suitable values for N may comprise those lengths typically associated with LCRs, e.g., 10-300 kb. Further filtering may be needed to remove redundant entries. The result is a list of homologous sequences, associated with positions in the chromosome at which they occur.

Homologous segments could also be identified by previously existing annotations. Many repetitive regions of the genome have been well characterized and their annotations are often freely available as metadata for a published reference genome (e.g., the GRCH38/hg38 reference genome and associated tracks available on the UCSC Genome Browser). Other software may also be used to identify repetitive regions (e.g., RepeatMasker).

In any case, once a set of paired homologous sequences is identified, the difference in base pairs is calculated between each pair of positions at which they occur. Those pairs are separated by a distance between 10 and 50 kb. These pairs are candidates for NAHR events. The disclosure recognizes that one or more predicted results of the candidate NAHR event (e.g., a deletion, duplication, inversion) may then be added as an alternative path to in the reference genome (i.e., the genomic reference 201) to account for that event.

This middle portion of FIG. 4 illustrates one way that, having identified the first segment 403 and the second segment 409 that are homologous to each other, the reference genome 201 may be segmented to facilitate in creating 117 an object connecting the first segment to the second segment. As shown, the reference genome 201 has been divided into five segments, representing the 5' sequence before the first segment 403, the first segment 403, the intervening sequence, the second segment 409, and finally the 3' sequence after the second segment. This segmentation has been chosen for ease of illustration and may differ in different embodiments; for example, one could also segment the genomic reference sequence 201 into three segments, representing the 5' sequence upstream of the intervening sequence, the intervening sequence itself, and the 3' sequence downstream of the intervening sequence. One may also choose to select different positions for which to divide the homologous segment; for example, because NAHR events may not occur precisely at the endpoints of LCRs, the midpoint of the homologous sequence may instead be chosen to guide segmentation.

The bottom portion of FIG. 4 shows a reference graph 401 generated by creating objects to store each of the segments of the reference sequence 201. The reference graph 401 includes nodes 415 connected by edges 419, and segments of the genomic reference 201 are stored in the edges 419. Alternatively, sequences can be stored in nodes as is discussed in greater detail below. As shown, an object 499 has been created to connect objects associated with the first segment 403 and the second segment 409. The object 499 creates an alternative path (representing a deletion) that may be followed through the reference graph 401, which corresponds to a predicted NAHR event.

While in this example the reference sequence 201 has been transformed into a reference graph 401, in preferred embodiments, the starting reference is itself a graph that includes known human genetic variation. For example, the reference sequence 201 may represent a single object in a larger graph structure, which is then segmented and re-connected to accommodate the predicted variation. In a genomic reference graph, nodes are connected by edges with sequence data stored in those objects, either in the nodes, the edges, or both. A known sequence is represented by a path through those connected nodes. Human genetic variation is represented by divergent paths through the graph (i.e., the paths converge where human genetic material is conserved and diverge to describe variants). For background, see U.S. Pub. 2015/0057946, incorporated by reference. In some preferred embodiments, a genomic reference graph is implemented as a DAG, but the acyclic requirement may be ignored and the reference may be implemented as a directed graph more generally.

Methods of the invention may operate using a reference genomic graph structure that includes known human variations. Alternately, methods may use a linear reference structure having no known human variations, e.g., containing only the reference sequence as a "backbone" branch. For each candidate NAHR event, an object 499 is inserted into the reference graph structure 401. The object 499 is an edge that connects a first position (of the first LCR, represented by the first segment 403) to a second position (of the second LCR, represented by the second segment 409). The positions selected may vary depending on the expected type of event; for example, and as shown in FIG. 4, if the event is an NAHR deletion then one may choose the positions to be the after the last base of the corresponding LCR. The edge object 499 thus represents a deletion of the intervening sequence 481 that would be removed if such an NAHR event had occurred. (Of course, if sequence data is instead associated with the edges of the graph, a vertex may be added that represents the deletion.)

Thus, the system 301 stores the genomic reference graph 401 as one or more objects in the tangible, non-transitory memory 375 coupled to a processor. The system further includes instructions that, when executed by the processor, cause the system to identify 109 within the genomic reference, using the processor, a first segment 403 and a second segment 409 that are homologous to each other and to create 117 an object connecting the first segment 403 to the second segment 409 and store the object in the memory 375.

Figure 5:
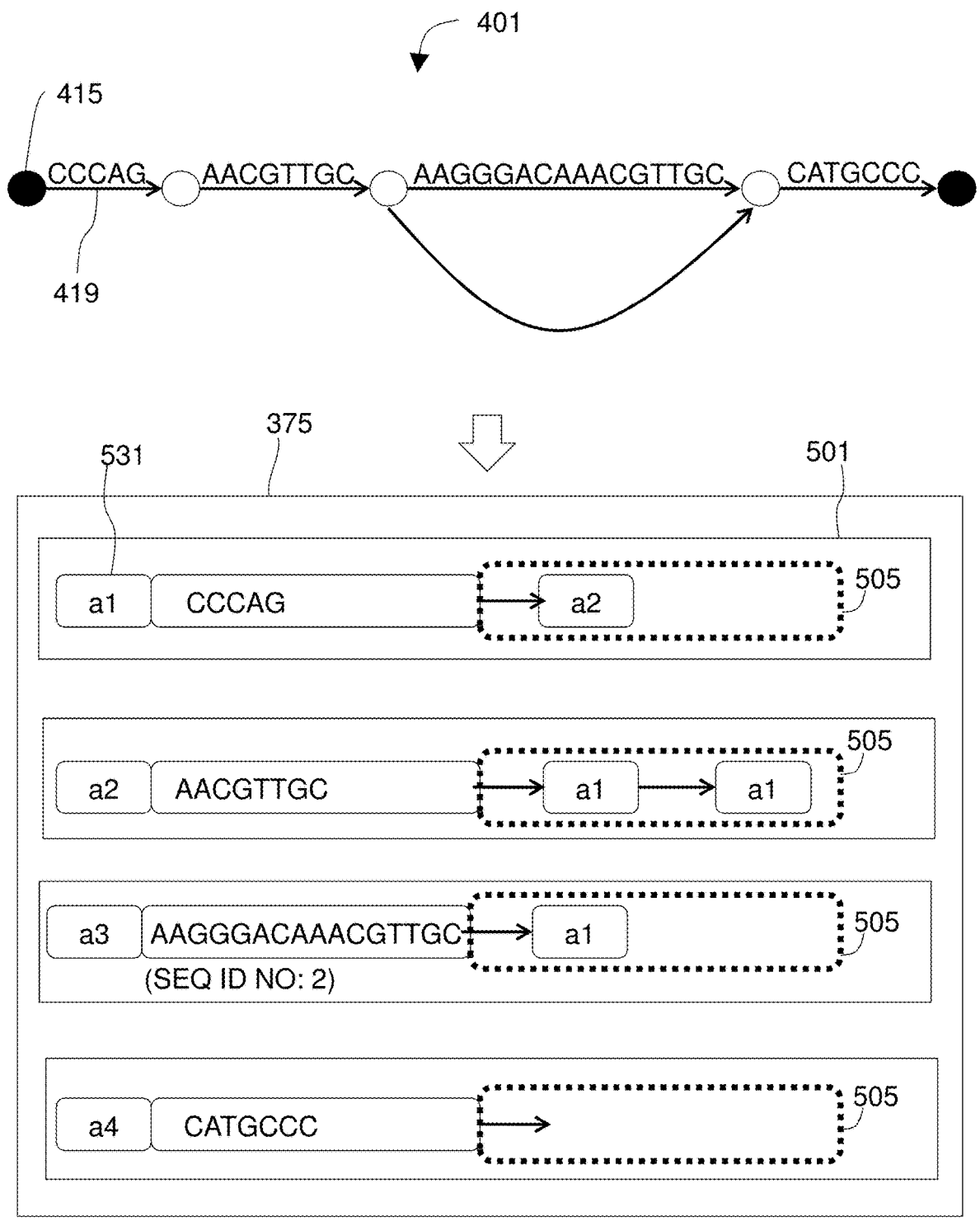
FIG. 5 illustrates creating objects to store a reference graph.

FIG. 5 illustrates how the system 301 creates objects associated with the reference graph 401, such as the object 499 of FIG. 4. The reference graph 401 includes nodes 415 connected by edges 419. In the memory 375, the system writes an object 501 for each edge. Each object 501 is located at a specific spatial address 531. Included in each object is a string of nucleotide characters associated with the corresponding edge 419 in the reference graph 401, as well as an adjacency list 505 that gives the spatial address 531 of each object to which that object is adjacent.

In computer science, a pointer is a programming language object, whose value refers to (or "points to") another value stored elsewhere in the computer memory using its memory address. Memory addresses may be fixed-length sequences of digits conventionally displayed and manipulated as unsigned integers. A digital computer's memory, more specifically main memory, consists of many memory locations, each having a physical address, a code, which the CPU (or other device) can use to access it. Most application programs do not have a knowledge of physical addresses. Rather, they address logical addresses, or virtual addresses, using the computer's memory management unit and operating system memory mapping. Using adjacency lists 505, the system takes advantage of having knowledge of the physical address. The processor can read from one object 501 and directly to an adjacent object without referring to an index or look-up table or other such logical, virtual construct. Thus, the object 499 connects the first segment 403 to the second segment 409 in reference graph 401 and is implemented as an object 501 in which the adjacency list 505 provides a direct connection from the first segment 403 to the second segment 409.

The reference graph 401 includes nodes 415 connected by edges 419, and segments of the genomic reference 201 are stored in the edges 419. Each edge gets instantiated as an object 501 in the memory 375. Other embodiments are included. For example, segments of the genome can be stored in nodes. In another example, nodes and edges can each get instantiated as objects. An important point is that the reference graph 401 may be populated with new connections. Specifically, possible NAHR events are being predicted and the reference graph 401 is modified to model those events by writing to objects in the memory 375.

In other embodiments, the reference graph may be stored as a set of objects, each object having a set of parent objects, an identifier, and an associated sequence. In still further embodiments, the reference graph may be stored as a topology, in which each object similarly has an identifier and an associated sequence.

Once the reference graph structure 401 is populated with all possible NAHR deletion events according to the used parameters, the reference graph 401 is used for the alignment of a subject sequence such as sequence reads from next-generation sequencing data. Patients who have a previously unknown NAHR deletion will have sequence reads that uniquely map to the edges representing that deletion, thus identifying the deletion event with high precision.

Figure 6:
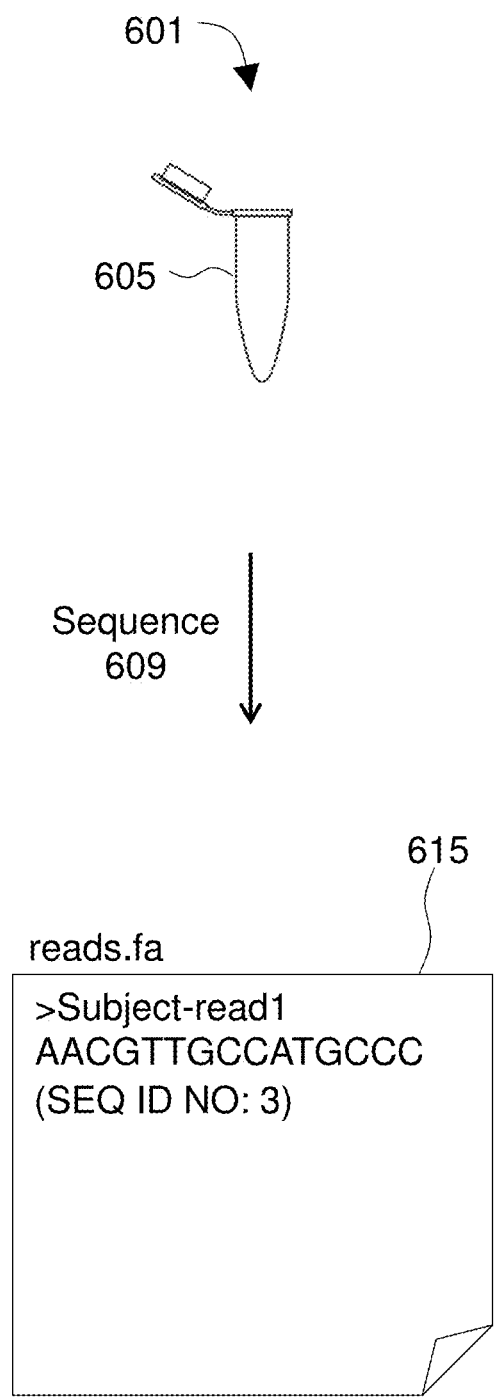
FIG. 6 illustrates obtaining sequences from a sample from a subject.

FIG. 6 illustrates obtaining 601 sequences 615 from a sample 605 from a subject. As a preliminary step (not depicted), nucleic acid may be isolated and/or enriched.

In certain embodiments, sequence reads are obtained by performing sequencing 609 on a sample 605 from a subject (however in some embodiments, sequence reads are obtained when a read file is transferred into a system of the invention). Sequencing may be by any method and sequencing instrument known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems and sequencing instruments sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, each incorporated by reference. 454 sequencing involves two steps. First, DNA is sheared into blunt-end fragments attached to capture beads and then amplified in droplets. Second, pyrosequencing is performed on each DNA fragment in parallel. Addition of nucleotides generates a light signal that is recorded by a CCD camera in a sequencing instrument.

Another example of a DNA sequencing technique and instrument that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

Sequencing 609 generates a plurality of sequences 615, which may be in the form of sequence reads. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 123 in a format such as FASTA, FASTQ, or similar.

Figure 7:
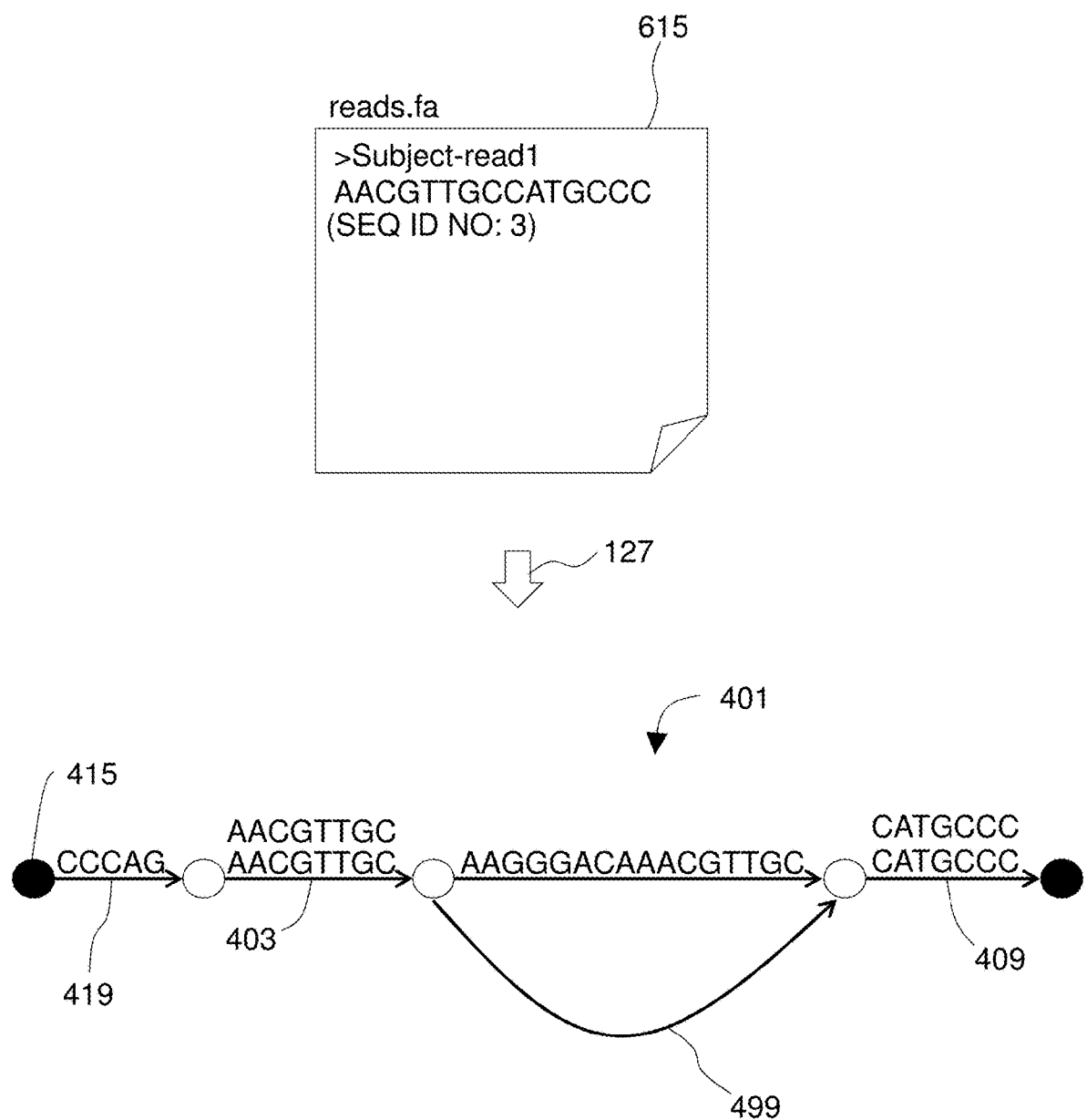
FIG. 7 shows aligning the sequences to a reference graph.

FIG. 7 illustrates finding 127 alignments between the sequences 615 and the reference graph 401. Using alignment operations of the invention, reads can be rapidly mapped to the reference graph 401 despite their large numbers or short lengths. Numerous benefits obtain by using a graph as a reference. For example, aligning against a graph is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference graph is provided here as an extension of pairwise alignment methods.

Pairwise alignment generally involves placing one sequence along part of target, introducing gaps according to an algorithm, scoring how well the two sequences match, and preferably repeating for various positions along the reference. The best-scoring match is deemed to be the alignment and represents an inference of homology between aligned portions of the sequences. In some embodiments, scoring an alignment of a pair of nucleic acid sequences involves setting values for the probabilities of substitutions and indels. When individual bases are aligned, a match or mismatch contributes to the alignment score by a substitution score, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affect the resulting alignment. Particularly, the relationship between the gap penalties and substitution probabilities influences whether substitutions or indels will be favored in the resulting alignment.

A pairwise alignment, generally, involves—for sequence Q (query) having m characters and a reference genome T (target) of n characters—finding and evaluating possible local alignments between Q and T. For any $1 \le i \le n$ and $1 \le j \le m$, the largest possible alignment score of T[h . . . i] and Q[k . . . j], where $h \le i$ and $k \le j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. One exact algorithms is referred to as Smith-Waterman (J Mol Biol, 147(1):195-197, 1981; Adv. in Math. 20(3), 367-387, 1976, both incorporated by reference). The original Smith-Waterman (SW) algorithm aligns linear sequences by rewarding overlap between bases in the sequences, and penalizing gaps between the sequences. The original SW algorithm is expressed for an nxm matrix H, representing the two strings of length n and m, in terms of equation (1):

$$H\_k0 = H\_0l = 0 \text{ (for } 0 \le k \le n \text{ and } 0 \le l \le m)$$

$$H\_ij = \max\{H\_(i-1, j-1) + s(a\_i, b\_j), H\_(i-1, j) - W\_in, H\_(i, j-1) - W\_del, 0\} \text{ (for } 1 \le i \le n \text{ and } 1 \le j \le m) \quad (1)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 < j \le m, 0 < k \le n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \text{MISMATCH\_PEN, if } S[j] \ne A[k] = \max(p[j-1,k-1], i[j-1,k-1], d[j-1,k-1]) + \text{MATCH\_BONUS, if } S[j] = A[k] \quad (3)$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0]element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH BONUS: 10
MISMATCH PEN: −20
INSERTION PEN: −40
OPENING PEN: −10
DELETION PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through the reference graph 401. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a reference graph 401 with the use of spatial memory addresses (e.g., native pointers or index-free adjacency) improves what the computer system is capable of, facilitating whole genomic scale analysis to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its object, the letter preceding d in its object is its (only) predecessor;

(ii) If d is the first letter of the sequence of its object, the last letter of the sequence of any object that is a parent of d's object is a predecessor of d.

The set of all predecessors is, in turn, represented as P[d].

In order to find the "best" alignment, the algorithm seeks the value of M[j,d], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d]=\max\{a,i,e,0\}$$

where $$e=\max\{M[j,p^*]+\text{DELETE\_PEN}\} \text{ for } p^* \text{ in } P[d]$$

$$i=M[j-1,d]+\text{INSERT\_PEN}$$

$$a=\max\{M[j-1,p^*]+\text{MATCH\_SCORE}\} \text{ for } p^* \text{ in } P[d],$$
if $S[j]=d;$ $$\max\{M[j-1,p^*]+\text{MISMATCH\_PEN}\} \text{ for } p^* \text{ in } P[d],$$
if $S[j]\neq d$ \hfill (6)

As described above, e is the highest of the alignments of the first j characters of S with the portions of the graph up to, but not including, d, plus an additional DELETE_PEN. Accordingly, if d is not the first letter of the sequence of the object, then there is only one predecessor, p, and the alignment score of the first j characters of S with the graph (up-to-and-including p) is equivalent to M[j,p]+DELETE_PEN. In the instance where d is the first letter of the sequence of its object, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its object, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its object, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p1] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for aligning sequences 615 to the reference graph 401 by calculating not only the insertion, deletion, and match scores for that element, but looking backward (against the direction of the graph) to any prior nodes on the graph to find a maximum score. For information see U.S. Pub. 2015/0227685 and U.S. Pat. No. 9,092,402, both incorporated by reference.

Figure 8:
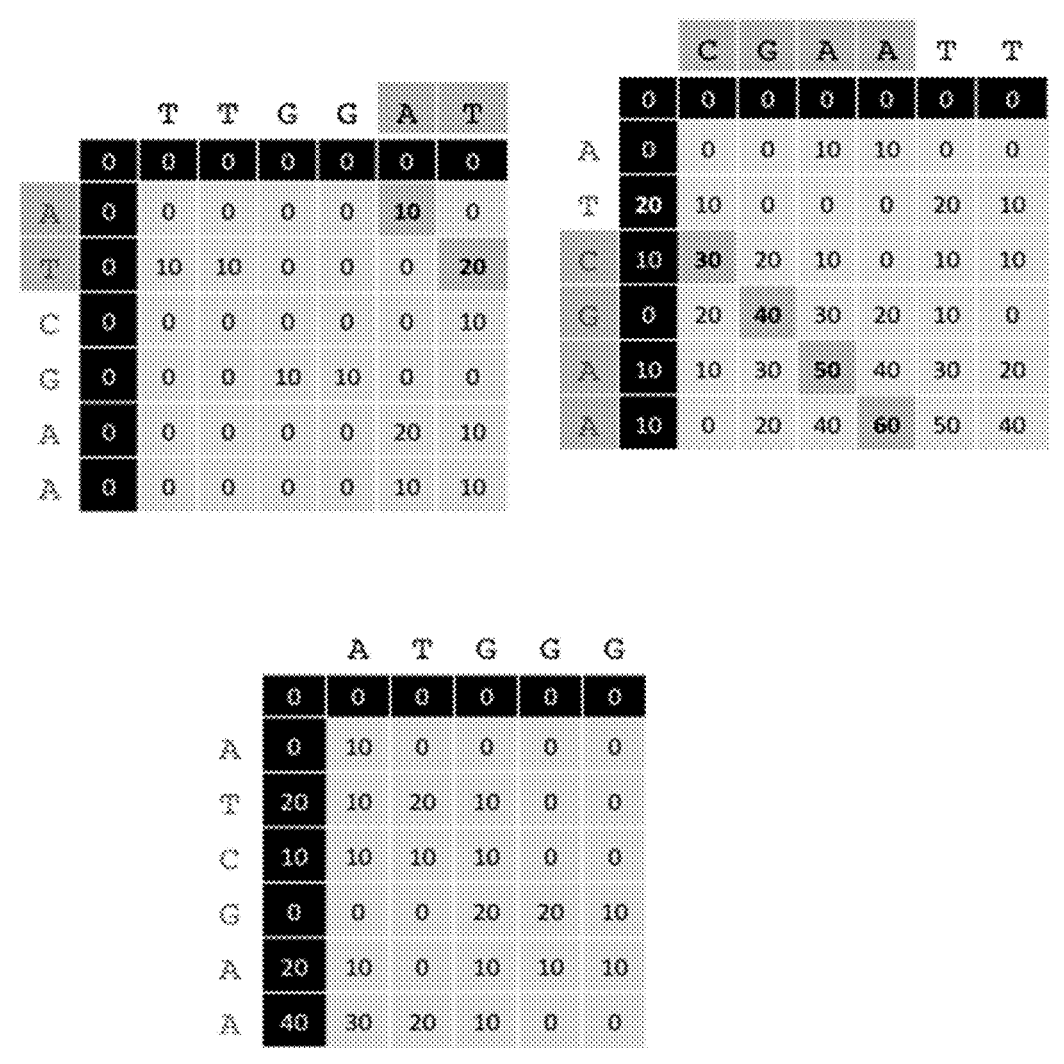

FIG. 8 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99 and Lee, 2003, Generating consensus sequences from partial order multiple sequence alignment graphs, Bioinformatics 19(8):999-1008, both incorporated by reference.

It may be found that the sequences 615 align to the reference graph 401 across (i.e., overlapping) the object 499 that was created to connect the first position (at the beginning of the first segment 403) to the second position (at the end of the second segment 409), as shown in FIG. 7. Because that alignment overlaps the edge object 499, it may be surmised that the corresponding segment of genetic information has been deleted from the subject's genome, relative to the reference.

Figure 9:
FIG. 9 shows providing a report describing a recombination event in the subject.

FIG. 9 shows providing a report 1001 describing a recombination event in the subject when the sequences align across the object. In the depicted embodiment, the report 1001 identifies Del 22q11.2 as a 3 mb deletion from the subject's genome. Additionally, the report 1001 identifies DG/VCF syndrome as a medical condition associated with the deletion. More generally, the report 1001 may identify a deletion or other recombination, a medical condition associated with the recombination, or both.

Use of systems and methods described herein provide a variety of benefits. Reference graphs according to the disclosure have many benefits when used for identifying previously unknown variations in patients. As in other situations, reference graphs are ideal objects against which to align. Performing alignments with a reference graph constructed with NAHR events is much more effective than attempting to identify an NAHR event after alignment to a traditional linear reference. The resulting graph can be used to quickly and accurately identify NAHR events with high precision, serving as an important medical research and diagnostic tool.

The reference is pre-populated with candidate deletions based on homologous segments. The homologous segments may be identified by analysis of intrinsic properties of the sequence of the reference. Additionally or alternatively, the first segment and the second segment are identified from a database of known repeats. Thus systems and methods may be used to find a plurality of low copy repeats, each low copy repeat comprising a pair of homologous segments, and create an additional object in the genomic reference connecting each pair of homologous segments.

As discussed above, storing sequence in edges of a graph is one embodiment. Other embodiments are included.

Figure 10:
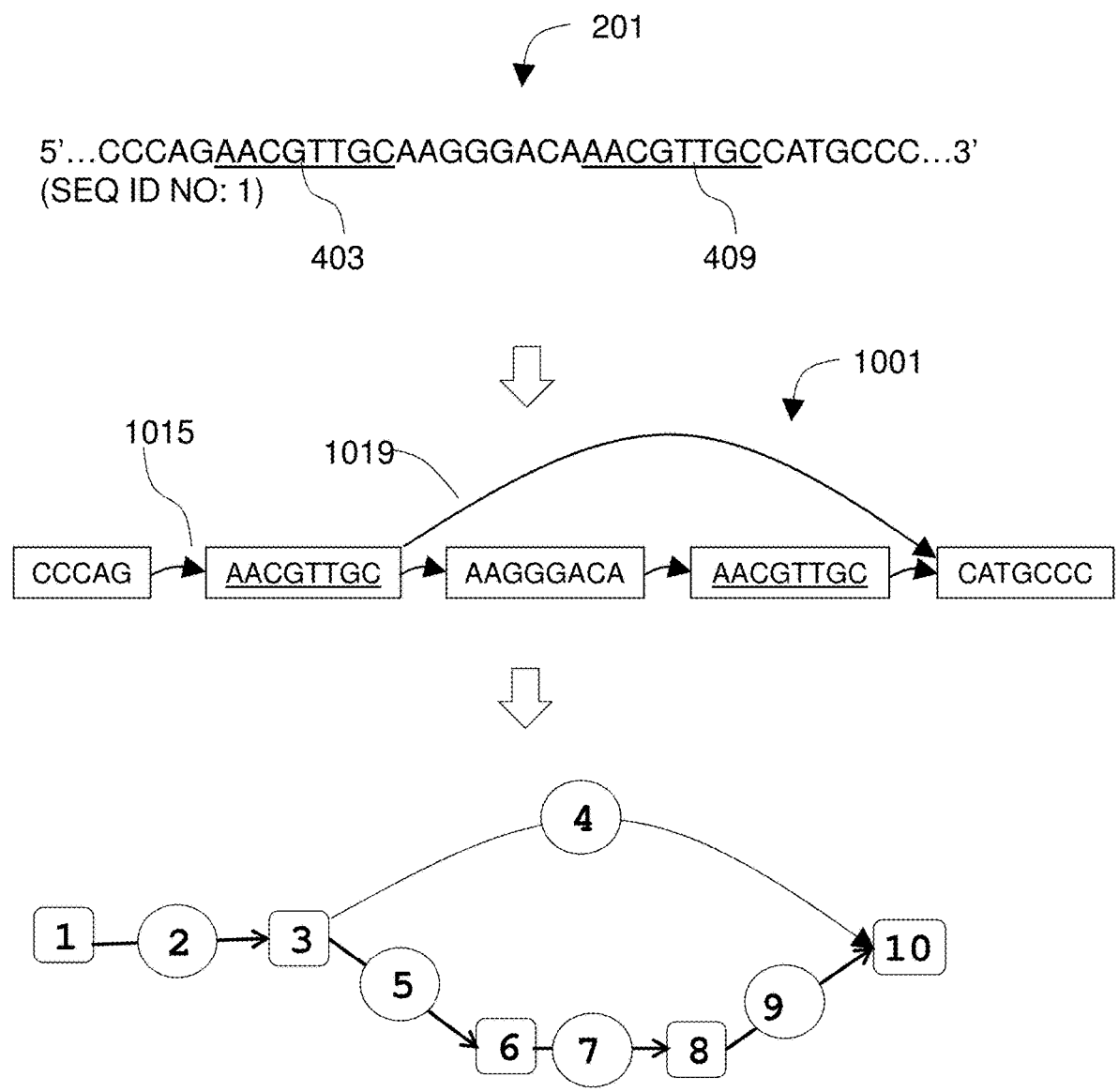
FIG. 10 shows storing strings within nodes.

FIG. 10 illustrates an embodiment in which strings of sequence data are stored in nodes. Starting with reference 201, a graph 1001 is made that includes nodes 1015 and edges 1019. Strings of characters representing segments of the reference 201 are stored in the nodes.

In some embodiments, each of the nodes 1015 and the edges 1019 are both stored as objects in memory 375. The bottom of FIG. 10 shows that each node and edge has been assigned a number for reference.

Figure 11:
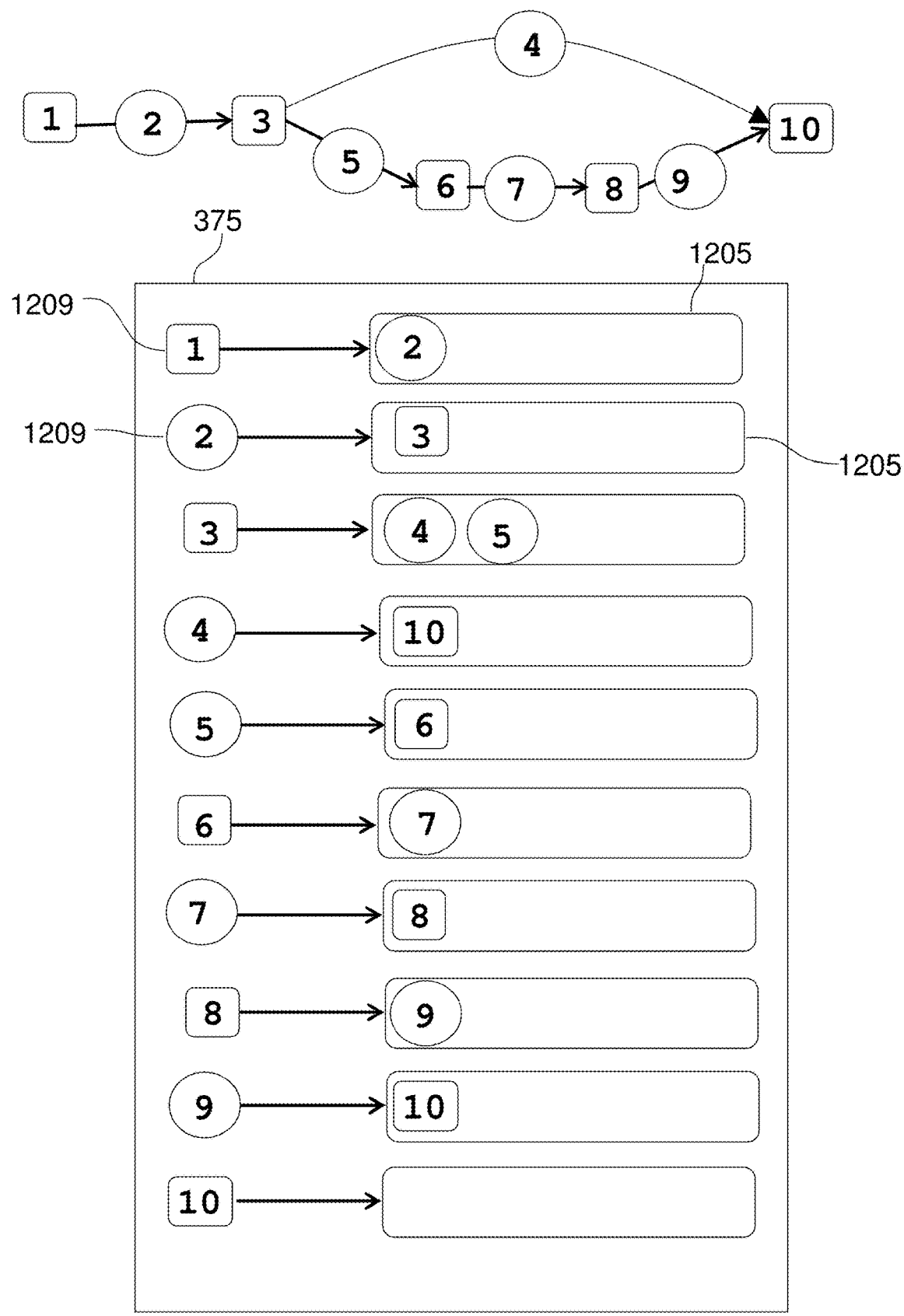
FIG. 11 shows that objects may be created for nodes and edges.

FIG. 11 also shows that objects may be created for nodes and edges. Creating objects for nodes and edges is a concept that is unlinked to the question of whether to store sequence data in nodes or edges. Each node and edge is instantiated as an object 1209 in the memory 375. Each object includes an adjacency list 1205 indicating those objects that are adjacent.

Embodiments of the invention include an operation for detecting homologous segments in the reference. A pair of homologous segments may be found by reading a segment of the reference and aligning that segment back to the reference to find good alignments other than the segment itself. For example, any part of the reference to which the segment aligns with at least 90% sequence similarity may be deemed to be a homologous segment.

FIG. 12 shows that in the method 101, identifying 109 homologous segments may include reading a string of length=N bases (here, N=8) from the genomic reference and aligning the string to the genomic reference to determine that the first segment is homologous to the second segment. This operation may be iterated for all or substantial portions of the reference 201. I.e., the N bases may be treated as a sliding window and may be pushed down the genome after each iteration. Thus, the method 101 may include reading a second string of bases offset along the genomic reference from the string of N bases and performing an alignment between the second string of bases and the genomic reference. The method may include iteratively sliding a window of length N to a plurality of positions along the genomic reference and, for each position, finding alignments between a string from a current position and the genomic reference. Preferably, each position is offset from the previous position by a fixed distance such as, for example, 1, n/2, or n. As previously noted, pairs of segments may also be found using other measures, such as from dot plots and partial alignments generated by aligning a nucleotide sequence (such as portions of a reference genome) against itself.

A pair of segments with at least 90% identity may be deemed to be homologous. Throughout most of biology, actual homology is unknowable but the distinction between identity by homology and identity by chance or convergent evolution is moot, because the NAHR mechanism is indifferent to the cause of the similarity. It is enough that the two segments are sufficiently similar.

Systems and methods have been described for detecting NAHR events in the genome of a subject. An important feature is populating the reference with predicted, possible NAHR events. Stated more generally, a reference may be populated with predicted, possible mutational events. Populating a reference with a predicted or possible mutational event may be taken to mean manipulating the reference to have a form consisting with the predicted or possible mutational event while also having a form consistent with a wild type. Where a mutation is known to be associated with a disease or condition, this suggests a method of screening for a disease.

Figure 13:
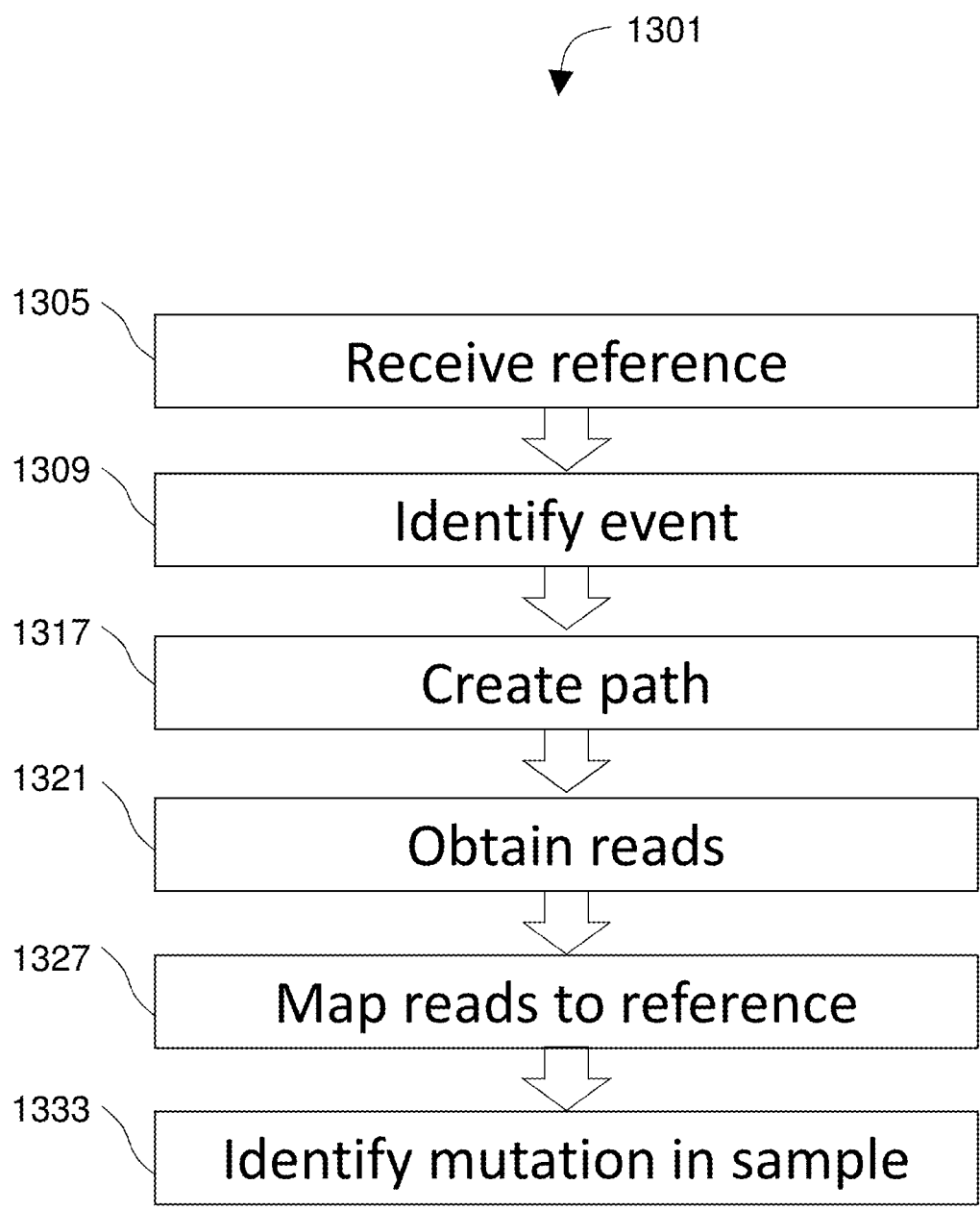
FIG. 13 diagrams steps in a method of screening for disease in a sample.

FIG. 13 diagrams steps in a method 1301 of screening for disease in a genomic sample. The method 1301 includes using at least one computer hardware processor for receiving 1305 a representation of a reference genome. The reference genome includes a sequence of symbols, the receiving comprising storing the reference genome in at least one object in computer memory. The method includes identifying 1309 the presence of a predicted mutational event in a location of the reference genome. An alternative path is created 1317 by the processor in the reference genome representing the predicted mutational event. The alternative path is created by segmenting the reference genome at the location of the predicted mutational event, creating a first path connecting the segmented reference genome, and creating a second path connecting at least part of the segmented reference genome with the predicted mutational event. A plurality of sequence reads is obtained 1321 from a genomic sample from a subject. At least one sequence read covers at least a portion of a mutation in the subject, corresponding to the predicted mutational event. The sequence reads are mapped 1327 to the reference genome via an operation that includes determining a location on the reference genome for which a score for the at least one sequence read is maximized, such that the determined location of the mapped at least one sequence read spans the alternate path representing the predicted mutational event. The computer hardware processor identifies 1333 the predicted mutational event as present in the genomic sample. Preferably, identifying the presence of a predicted mutational event in a location of the reference genome comprises accessing information specifying the presence of the predicted mutational event (e.g., by accessing a database of predicted mutations, predicting the presence of the mutational event, or both). In certain embodiments, the predicted mutational event is determined computationally by scanning the reference genome. Predicting the presence of the mutational event may include identifying a first segment of the reference genome and a second segment of the reference genome that are homologous (e.g., 90% sequence similarity, separated by a distance of between 10 kilobases and 300 kilobases, or both).

In some embodiments, segmenting the reference genome at the location of the predicted mutational event is done by segmenting the reference genome into a first segment, a second segment, and a third segment, and associating each of the segments with respective first, second, and third objects in computer memory. An alternative path is created in the reference genome representing the predicted mutational event, which may include associating the predicted mutational event with a fourth object in computer memory. A first path is created connecting the segmented reference genome comprises connecting the first, second, and third objects into the first path. A second path is created connecting at least part of the segmented reference genome with the predicted mutational event comprises connecting the first, fourth, and third objects into the second path. Preferably the first segment and the third segment are homologous. The second path may represent a deletion of the second segment. The second path may represent a recombination event in the reference genome. The method may include identifying a medical condition in the genomic sample associated with the predicted mutational event. In some embodiments, the representation of the reference genome is a directed acyclic graph.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of detecting a non-allelic homologous recombination (NAHR), the method comprising:
   accessing, by a computer system, a genomic reference stored in the computer system and including information specifying a graph having a plurality of nodes and edges, the nodes representing nucleotide sequences, wherein the plurality of nodes and edges is stored as a plurality of objects in a memory of the computer system, wherein a first object in the plurality of objects stores a list of pointers specifying one or more locations in the memory at which at least one other object in the plurality of objects is stored, wherein the at least one other object is adjacent to the first object in the graph;
   identifying within the genomic reference a first pair of homologous nucleotide sequences;
   modifying the genomic reference to include a new object connecting the first pair of homologous nucleotide sequences and storing the new object in the memory, wherein the new object specifies at least a part of a new path through nodes of the graph and indicates a nucleotide sequence that results from a predicted NAHR event, the new object including a pointer to an object, among the plurality of objects, representing one of the first pair of homologous nucleotide sequences;
accessing a sample nucleotide sequence associated with a subject;
aligning the sample nucleotide sequence from the subject to the first pair of homologous nucleotide sequences using the new object indicating the nucleotide sequence that results from the predicted NAHR event; and
determining, based on results of the aligning, whether the sample nucleotide sequence is indicative of a NAHR event in the subject.

2. The method of claim 1, wherein the graph is a directed acyclic graph.

3. The method of claim 2, wherein aligning the sample nucleotide sequence to the first pair of homologous nucleotide sequences comprises assigning a score to each of a plurality of paths through the first pair of homologous nucleotide sequences in the genomic reference modified to include the new object.

4. The method of claim 1, further comprising: sequencing nucleic acid from the subject to generate a sequence read.

5. The method of claim 1, wherein identifying the first pair of homologous nucleotide sequences comprises determining whether nucleotide sequences of the first pair have at least about 90% sequence similarity.

6. The method of claim 5, wherein identifying the first pair of homologous nucleotide sequences comprises determining whether nucleotide sequences of the first pair are separated by a distance between 10 kilobases and 300 kilobases.

7. The method of claim 1, further comprising identifying the first pair of homologous nucleotide sequences from a database of known repeats.

8. The method of claim 1, further comprising:
identifying a plurality of low copy repeats, each low copy repeat comprising a pair of homologous nucleotide sequences, and
modifying the genomic reference to include, for a first low copy repeat of the identified plurality of low copy repeats, a second new object connecting the associated pair of homologous nucleotide sequences and storing the second new object in the memory.

9. The method of claim 1, wherein identifying the first pair of homologous nucleotide sequences comprises:
reading a set of nodes and edges associated with a string of N bases from the genomic reference; and
aligning the set of nodes and edges to the genomic reference to determine that nucleotide sequences of the first pair of homologous nucleotide sequences are homologous.

10. The method of claim 9, further comprising:
reading a second set of nodes and edges associated with a string of bases offset along the genomic reference from the string of N bases; and
aligning the second set of nodes and edges and the genomic reference.

11. The method of claim 10, further comprising:
iteratively searching a window of nodes and edges of length N at a plurality of positions of the genomic reference; and
for each position of the plurality of positions, aligning the second set of nodes and edges to a third set of nodes and edges of length N at the position of the genomic reference.

12. The method of claim 11, wherein each position of the plurality of positions is offset from a previous position by a fixed distance.

13. A computer system for detecting a non-allelic homologous recombination (NAHR), the computer system comprising:
at least one processor; and
at least one non-transitory computer-readable storage device storing processor-executable instructions that, when executed by the at least one processor, cause the at least one processor to perform:
accessing a genomic reference stored in the at least one non-transitory computer-readable storage device and including information specifying a graph having a plurality of nodes and edges, the nodes representing nucleotide sequences, wherein the plurality of nodes and edges is stored as a plurality of objects in a memory of the computer system, wherein a first object in the plurality of objects stores a list of pointers specifying one or more locations in the memory at which at least one other object in the plurality of objects is stored, wherein the at least one other object is adjacent to the first object in the graph;
identifying within the genomic reference a first pair of homologous nucleotide sequences;
modifying the genomic reference to include a new object connecting the first pair of homologous nucleotide sequences and storing the new object in the memory, wherein the new object specifies at least a part of a new path through nodes of the graph and indicates a nucleotide sequence that results from a predicted NAHR event, the new object including a pointer to an object, among the plurality of objects, representing one of the first pair of the homologous nucleotide sequences;
accessing a sample nucleotide sequence associated with a subject;
aligning the sample nucleotide sequence from the subject to the first pair of homologous nucleotide sequences using the new object indicating the nucleotide sequence that results from the predicted NAHR event; and
determining, based on results of the aligning, whether the sample nucleotide sequence is indicative of a NAHR event in the subject.

14. The computer system of claim 13, wherein the graph is a directed acyclic graph.

15. The method of claim 1, wherein the new object indicates a deletion of an intervening nucleotide sequence between the first pair of homologous nucleotide sequences.

16. The method of claim 1, wherein two objects in the plurality of objects represent the first pair of homologous nucleotide sequences.

17. The method of claim 16, the pointer is a pointer stored in a list of pointers in a first of the two objects and is a pointer to a physical location in the memory at which a second of the two objects is stored.

18. At least one computer readable storage device storing processor-executable instructions that, when executed by at least one processor, cause the at least one processor to perform:
accessing a genomic reference stored in the at least one non-transitory computer-readable storage device and including information specifying a graph having a plurality of nodes and edges, the nodes representing nucleotide sequences, wherein the plurality of nodes and edges is stored as a plurality of objects in a memory, wherein a first object in the plurality of objects stores a list of pointers specifying one or more locations in the memory at which at least one other object in the plurality of objects is stored, wherein the at least one other object is adjacent to the first object in the graph;

identifying within the genomic reference a first pair of homologous nucleotide sequences;

modifying the genomic reference to include a new object connecting the first pair of homologous nucleotide sequences and storing the new object in the memory, wherein the new object specifies at least a part of a new path through nodes of the graph and indicates a nucleotide sequence that results from a predicted NAHR event, the new object including a pointer to an object, among the plurality of objects, representing one of the first pair of homologous nucleotide sequences;

accessing a sample nucleotide sequence associated with a subject;

aligning the sample nucleotide sequence from the subject to the first pair of homologous nucleotide sequences using the new object indicating the nucleotide sequence that results from the predicted NAHR event; and determining, based on results of the aligning, whether the sample nucleotide sequence is indicative of an NAHR event in the subject.

19. The at least one computer readable storage device of claim 18, wherein the graph is a directed acyclic graph.

* * * * *